(12) United States Patent
Huang

(10) Patent No.: US 10,646,626 B2
(45) Date of Patent: May 12, 2020

(54) REDUCED-PRESSURE DEVICE

(71) Applicant: BenQ Materials Corporation, Taoyuan (TW)

(72) Inventor: Mao-Sung Huang, Taoyuan (TW)

(73) Assignee: BenQ Materials Corporation, Taoyuan (TW)

( * ) Notice: Subject to any disclaimer, the term of this patent is extended or adjusted under 35 U.S.C. 154(b) by 328 days.

(21) Appl. No.: 15/839,812

(22) Filed: Dec. 12, 2017

(65) Prior Publication Data
US 2018/0256791 A1 Sep. 13, 2018

(30) Foreign Application Priority Data

Mar. 9, 2017 (TW) .............................. 106203349 U

(51) Int. Cl.
| | |
|---|---|
| *A61M 1/00* | (2006.01) |
| *F04B 35/06* | (2006.01) |
| *F04B 35/01* | (2006.01) |
| *F04B 41/02* | (2006.01) |
| *F04B 37/10* | (2006.01) |
| *F04B 39/00* | (2006.01) |
| *F04B 53/10* | (2006.01) |

(52) U.S. Cl.
CPC ........ *A61M 1/0068* (2014.02); *A61M 1/0027* (2014.02); *A61M 1/0035* (2014.02); *A61M 1/0066* (2013.01); *F04B 35/01* (2013.01); *F04B 35/06* (2013.01); *F04B 37/10* (2013.01); *F04B 39/0022* (2013.01); *A61M 2205/0216* (2013.01); *A61M 2205/073* (2013.01); *A61M 2205/3344* (2013.01); *A61M 2205/583* (2013.01); *F04B 41/02* (2013.01); *F04B 53/10* (2013.01)

(58) Field of Classification Search
CPC .............. A61M 1/0068; A61M 1/0066; A61M 1/0027; A61M 1/0035; A61M 2205/0216; A61M 2205/073; A61M 2205/3344; A61M 2205/583; F04B 35/06; F04B 35/01; F04B 37/10; F04B 39/0022; F04B 41/02; F04B 53/10; F04B 9/14; F04B 33/00; F04B 33/005; F04B 19/22; F16F 9/00; F16F 9/0209; F16F 92/109
USPC ....................................................... 92/165 R
See application file for complete search history.

(56) References Cited

U.S. PATENT DOCUMENTS

| | | | | |
|---|---|---|---|---|
| 2007/0023365 A1* | 2/2007 | Liao | ........................ | F04B 33/00 210/776 |
| 2012/0071845 A1* | 3/2012 | Hu | ...................... | A61M 1/0068 604/319 |

* cited by examiner

*Primary Examiner* — Charles G Freay
*Assistant Examiner* — Christopher J Brunjes
(74) *Attorney, Agent, or Firm* — CKC & Partners Co., LLC

(57) ABSTRACT

A reduced-pressure device includes a housing having recesses on sidewalls thereof, an air pressure storage unit and a compression unit. The air pressure storage unit is installed in the housing and comprises a pressure storage container, a piston assembly and a piston spring, and the compression unit is mounted on the piston assembly. The compression unit further includes a pressing element and a turntable. The pressing element is accommodatable in the recesses of the housing, and rotatable by the turntable in relative to the air pressure storage unit and the housing, and when the pressing element is pulled out of the recesses and rotated to a predetermined position to compress the piston assembly to produce a negative pressure in the pressure storage container, the pressing element can be rotated back to the original position to be accommodated in the recesses again after using.

9 Claims, 11 Drawing Sheets

REDUCED-PRESSURE DEVICE

RELATED APPLICATIONS

This application claims the priority benefit of Taiwanese application serial no. 106203349, filed on Mar. 9, 2017, which is incorporated herein by reference.

BACKGROUND

Technical Field

The present disclosure relates to a reduced-pressure device for providing reduced-pressure to a negative-pressure wound dressing. Particularly, the present disclosure relates to a reduced-pressure device suitably for generating negative-pressure manually.

Description of Related Art

In recent years, with the advancement of medical technology, physicians often need to carry out surgery for patients. The surgery procedure will result in significant incision to the epidermis and the related tissues, and then the incision is closed with a U-shaped nails, a suture or an adhesive. When the skin has a wound, whether it is caused by surgery or accident, the normal wound healing process generally can be divided into three stages, respectively, inflammation stage, proliferation stage and remodeling stage, but the stages often overlap and interact with each other.

In the inflammatory stage, usually occurs in 0 to 3 days after the wound forming, vascular rupture causes red blood cells and blood to exudate into the tissues, and to reveal swelling and pain of inflammation. In the proliferative stage, usually occurs in 3 to 12 days after the wound forming, the wound mainly forms granulation tissues and epithelial cells. While in the remodeling stage, usually occurs in 6 to 12 months after the wound forming. Fibroblasts rely on microvascular for supplying oxygenation to result in consistent migration and to synthesize collagen matrix. The maturity and the tensile strength of collagen fibers reach the maximum in 2 to 3 weeks after the wound forming. With the maturity of collagen fibers, the collagen fibers gradually become scar tissues, and the epithelial cells are gradually mature and binding with the base membrane. Then the healing of the tissues is gradually formed.

If the wound is exposed to dirt, bacteria or other microorganism during the closure and healing of the wound, the wound healing time will be prolonged, and even the wound will worsen. Providing a device which can effectively accelerates the wound healing and reducing the amount of microorganism in order to avoid further infection is a common demand of the physicians and the patients.

SUMMARY

In accordance with the above-mentioned, the present disclosure provides a reduced-pressure device for the users to maintain the negative pressure of the negative-pressure wound dressing for wound treatment, thereby accelerating the healing of the wound.

The present disclosure provides a reduced-pressure device for wound treatment comprising a housing having recesses on sidewalls thereof, an air pressure storage unit installed in the housing, comprising a pressure storage container, a piston assembly slidably installed in the pressure storage container and a piston spring installed between the base of the pressure storage container and the piston assembly, and a compression unit mounted on the piston assembly of the air pressure storage unit, including a pressing element and a turntable, wherein for generating a negative pressure, the pressing element is pulled out of the recesses and rotated to a predetermined position to compress the piston assembly down to generate a negative pressure in the pressure storage container and the pressing element is pulled up and rotated back to the original position for being accommodated into the recesses.

In a reduced-pressure device of a preferred embodiment of the present disclosure, the compression unit further comprises a sliding element connected to the pressing element and to the turntable to stabilize the movement between the pressing element and the turntable and simultaneously rotate the turntable.

In a reduced-pressure device of another preferred embodiment of the present disclosure, the pressing element further includes a pair of push rods and a pressing portion connecting the push rods, wherein each of the push rods further comprises a first engaging portion and a second engaging portion, and the sliding element includes a cap and an extended shaft, wherein the cap has a pair of first positioning portions for engaging with the first engaging portion of each push rod, and the turntable includes a pair of second positioning portions for engaging with the second engaging portion of each push rod. When the first engaging portion of each push rods is coupled to the first positioning portion of the sliding element, the pressing element can pull the sliding element at the same time, and when the second engaging portion of each of the push rods is coupled to the second positioning portion of the turntable respectively, the pressing element can be prevented from being pulled out of the reduced-pressure device.

In a reduced-pressure device of another preferred embodiment of the present disclosure, the piston assembly further comprises a piston cover and a piston, and the piston cover have a pair of push rod openings for push rods of the pressing element. The push rods of the pressing element can pass through the push rod openings to push the piston of the piston assembly when the pressing element is positioned at the predetermined position.

In a reduced-pressure device of another preferred embodiment of the present disclosure, the air pressure storage unit further comprises a sealing element to seal the pressure storage container.

In a reduced-pressure device of another preferred embodiment of the present disclosure, the sealing element further comprises a check valve for connecting a connecting pipe.

In a reduced-pressure device of another preferred embodiment of the present disclosure, the sealing element further comprises a working indicator to indicate the negative-pressure state in the air pressure storage unit.

In a reduced-pressure device of another preferred embodiment of the present disclosure, the reduced-pressure device further comprises a pressure indicating module engaged to the pressure storage container and the piston assembly.

In a reduced-pressure device of another preferred embodiment of the present disclosure, the piston cover further comprises a transparent window to expose the pressure indicating module.

The pressing element of the present reduced-pressure device is accommodated in the recesses of the housing, and only when the air pressure storage unit needs to be evacuated to generate a negative pressure, the pressing element is pulled out, rotated to a predetermined position and pushed into the opening of the piston cover, and then return to be accommodated in the recesses. The present compression unit can effectively prevent from being worn-out and the aesthetics of the reduced-pressure device can be obtained. In addition, the working indicator enables the users easily to know the working condition of the current reduced-pressure device in a tactile manner. The pressure indicator module provides visual information that allows the user to know more about the remaining workability of the present reduced-pressure device. Users can always use the compression unit to generate a reduced-pressure state to keep the wound clean, and to accelerate the efficacy and speed of the wound healing.

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only typical embodiments of this disclosure and are therefore not to be considered limiting of its scope, for the disclosure may admit to other equally effective embodiments. The above and other aspects and advantages of the present disclosure will become apparent from the following detailed description of the present disclosure taken in conjunction with the drawings.

DETAILED DESCRIPTION

Figure 1A:
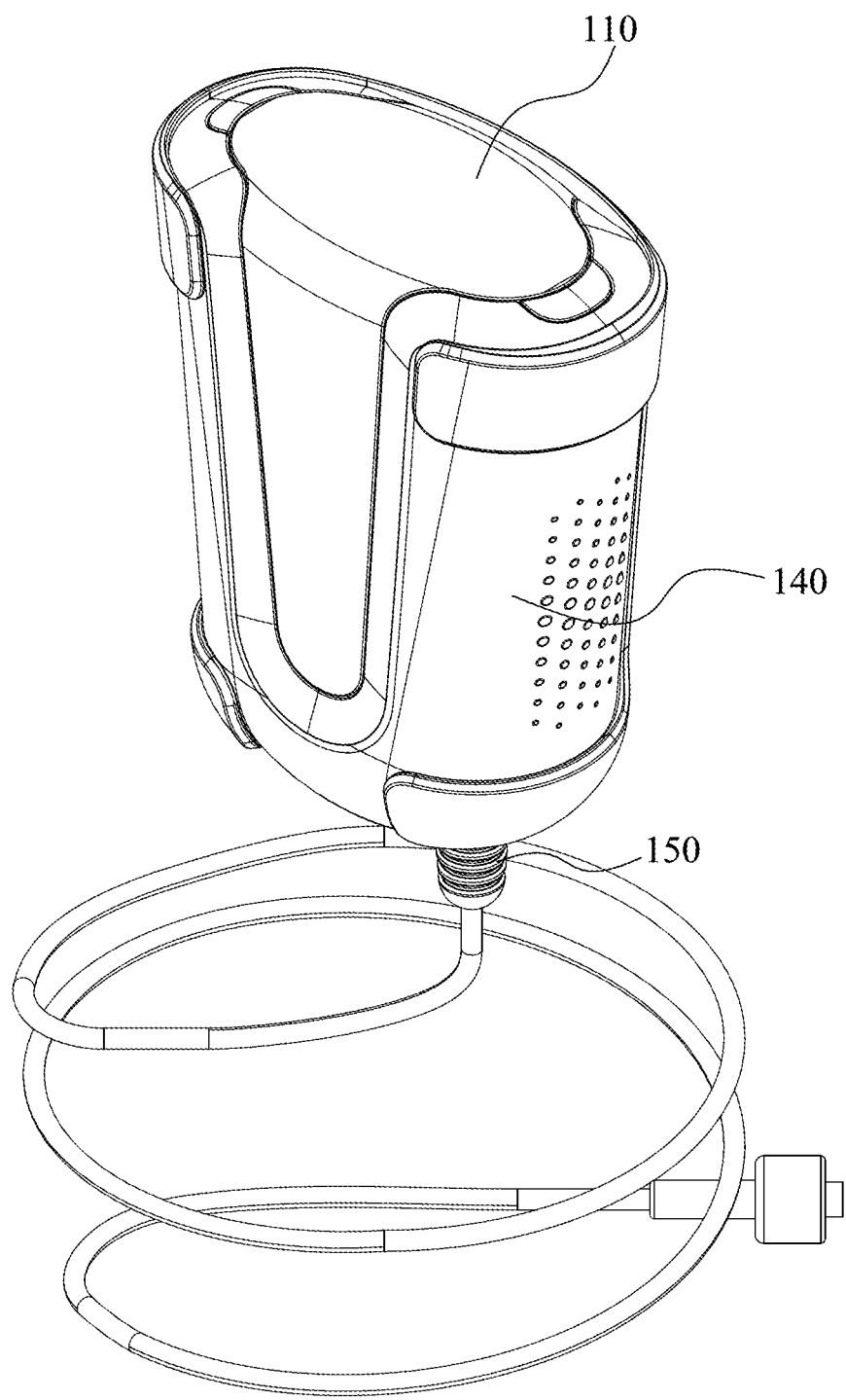
FIG. 1A shows a stereoscopic perspective view of a reduced-pressure device in accordance with an embodiment of the present disclosure.

Referring now to the drawings to illustrate the embodiments of the present reduced-pressure device. In the following embodiments of the present disclosure, the like elements refer to like symbols in the figures. The following description will introduce the embodiment of the above-described reduced-pressure device. For being better understood the embodiments of the present disclosure, a detailed description thereof is provided. However, well-known functions or constructions may not be described in detail for brevity and/or clarity. The drawings are not necessarily to scale, emphasis instead being placed upon illustrating the principles of the disclosure rather than to limit and restrict of the scope of the present disclosure defined in the appended claim.

The advantages and features of the present disclosure will become better understood with reference to the following more detailed description and claims taken in conjunction with the accompanying drawings. It should be understood that the exemplary embodiments of the present disclosure described below may be modified in many different ways without departing from the inventive principles disclosed herein, and the scope of the present disclosure is therefore not limited to these particular embodiments. Rather, these embodiments are provided so that this disclosure will be thorough and complete, and will fully convey the concept of the disclosure to those skilled in the art by way of example and not of limitation. In the drawings, the thickness of layers, films, and regions are exaggerated for clarity. The present disclosure is only defined by the appended claims.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein.

Figure 1B:
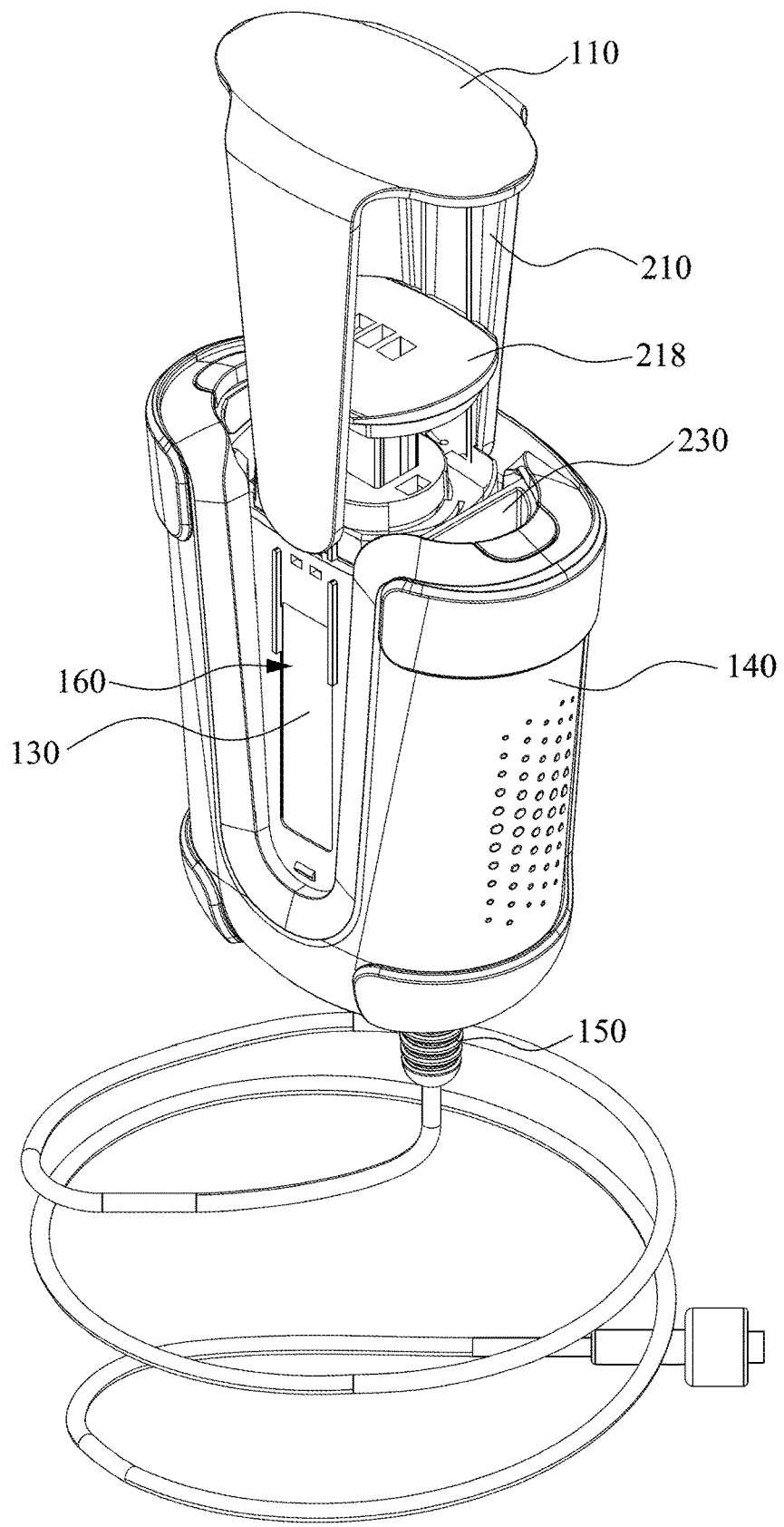
FIG. 1B shows a stereoscopic perspective view of a reduced-pressure device when the compression unit is pulled up in FIG. 1A.
Figure 1C:
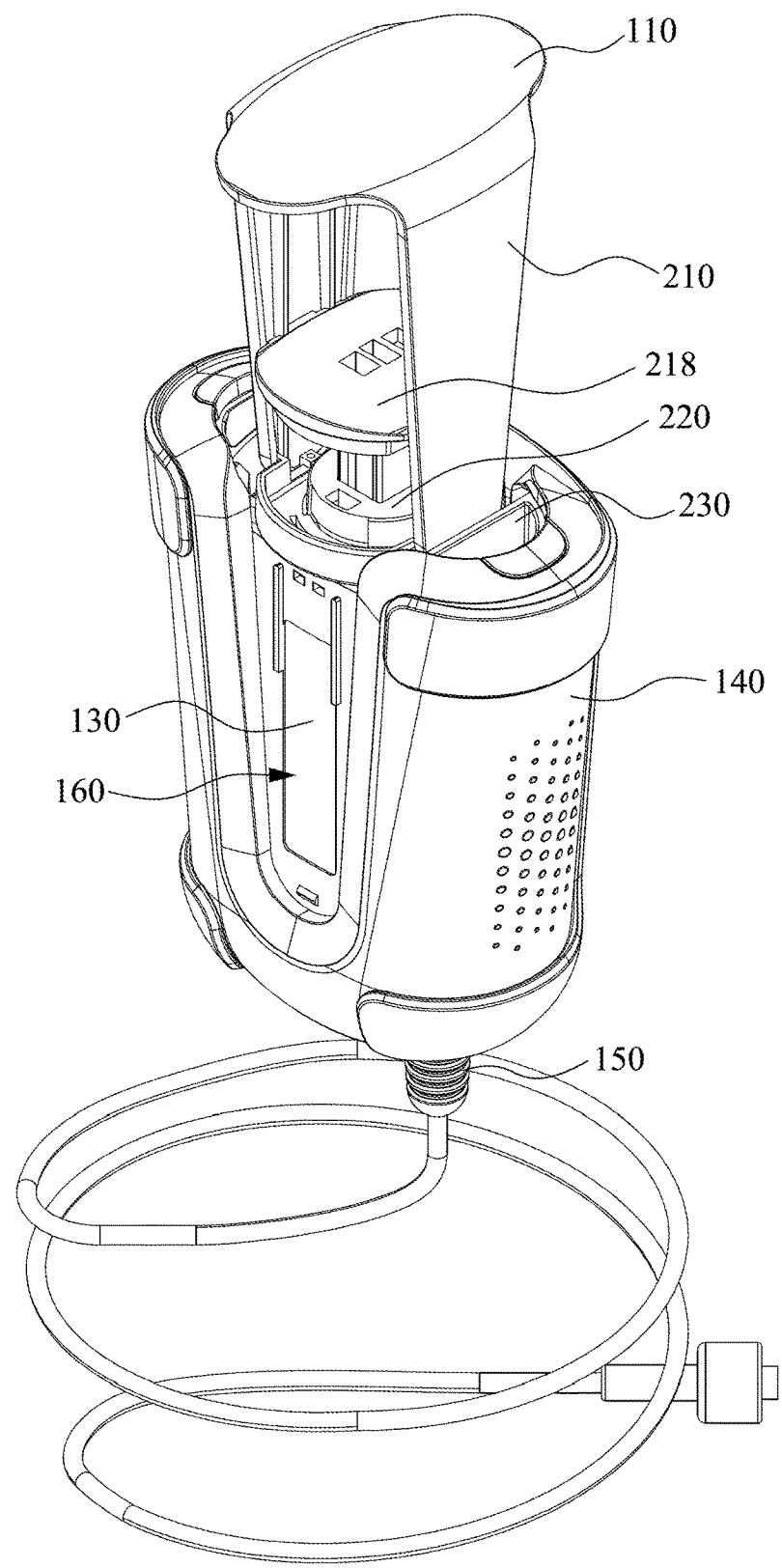
FIG. 1C shows a stereoscopic perspective view of a reduced-pressure device when the compression unit is rotated to a predetermined position in FIG. 1A.
Figure 1D:
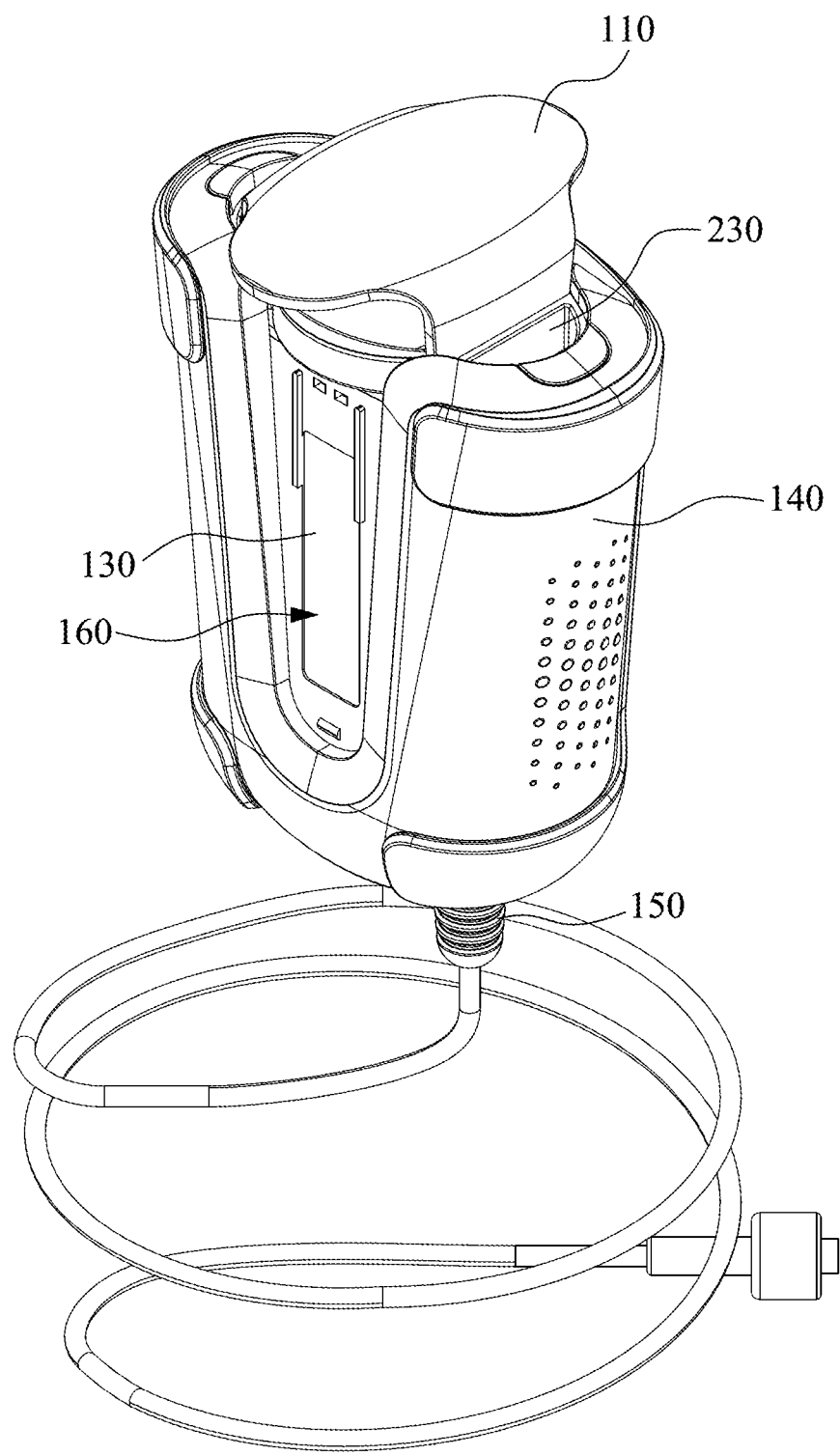
FIG. 1D shows a stereoscopic perspective view of a reduced-pressure device when the compression unit is pressed down to compress the air pressure storage unit in FIG. 1A.
Figure 2A:
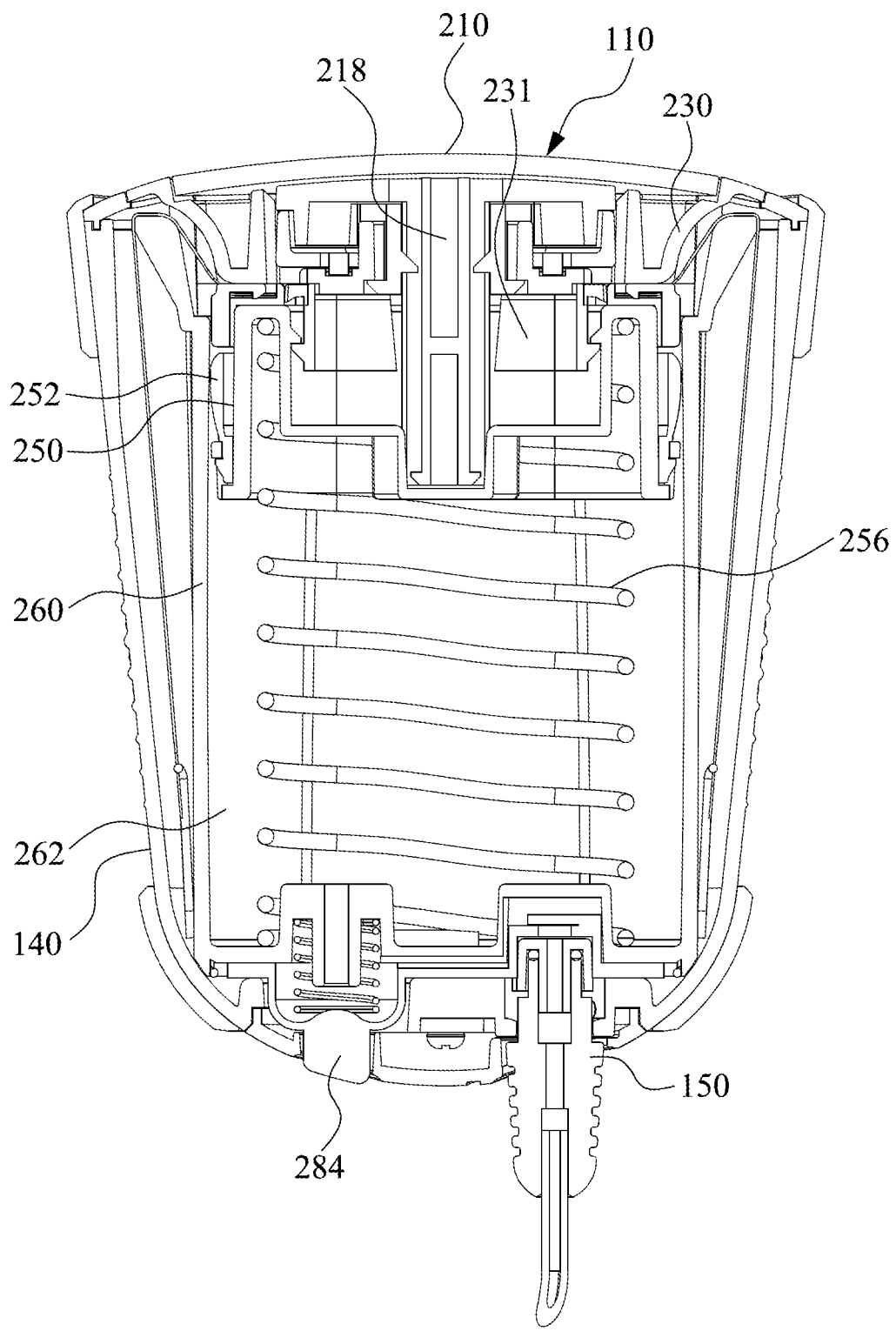
FIG. 2A shows a cross-sectional perspective view of a reduced-pressure device which is not yet started in accordance with an embodiment of the present disclosure.

Referring to FIG. 1A to FIG. 1D and FIG. 2A, FIG. 1A shows a perspective view of a reduced-pressure device in accordance with an embodiment of the present disclosure; FIG. 1B shows a perspective view of the reduced-pressure device when a compression unit is pulled up; FIG. 1C shows a perspective view of the reduced-pressure device when the compression unit is rotated to a predetermined position; FIG. 1D shows a perspective view of the reduced-pressure device when the compression unit is pressed down to compress the air pressure storage unit; FIG. 2A shows a cross-sectional perspective view of a reduced-pressure device which is not yet operated. The present disclosure provides a reduced-pressure device 100 for wound treatment comprising a housing 140 having recesses 160 on sidewalls thereof (only one recess is shown in the drawing), an air pressure storage unit 130 installed in the housing 140, comprising a pressure storage container 260, a piston assembly 250 installed in the pressure storage container 260 and a piston spring 256 installed between the base of the pressure storage container 260 and the piston assembly 250, and a compression unit 110 mounted on the piston assembly 250 of the air pressure storage unit 130, including a pressing element 210 and a turntable 220. The pressing element 210 is accommodatable in the recesses 160 of the housing 140, and rotatable by the turntable 220 in relative to the air pressure storage unit 130 and the housing 140, and when the pressing element 210 is pulled out of the recesses 160 and rotated to a predetermined position to compress the piston assembly 250 to produce a negative pressure in the pressure storage container 260. The pressing element 210 can be rotated back to the original position and be accommodated in the recesses 160 again after using. Accordingly, when the reduced-pressure device 100 is not in use or after generate a reduced pressure, the pressing element 210 of the compression unit 110 can be housed in the recesses 160 of the housing 140 without protruding from the housing 140. The present reduced-pressure device is easily to be carried and used.

As shown in FIG. 1B and FIG. 1C, the compression unit 110 of the reduced-pressure device 100 will be pulled up when used. The compression unit 110 further comprises a sliding element 218 comprising a cap 221 and an extended shaft 217, wherein the cap 221 is engaged to the pressing element 210 and the extended shaft 217 is engaged to the turntable 220 to stabilize the movement between the pressing element 210 and the turntable 220 and simultaneously rotate the turntable 220.

As shown in FIG. 1B to FIG. 1D and FIG. 2A, the pressing element 210 of the compression unit 110 is pulled up and rotated to a predetermined position, for example, in 90 degrees relative to the air pressure storage unit 130 and the housing 140 as shown in the drawings and is not limited thereto, to compress down the compression unit 110 and the sliding element 218 and at the same time, compress down the piston assembly 250 to produce a negative pressure in the air pressure storage unit 130.

Figure 3:
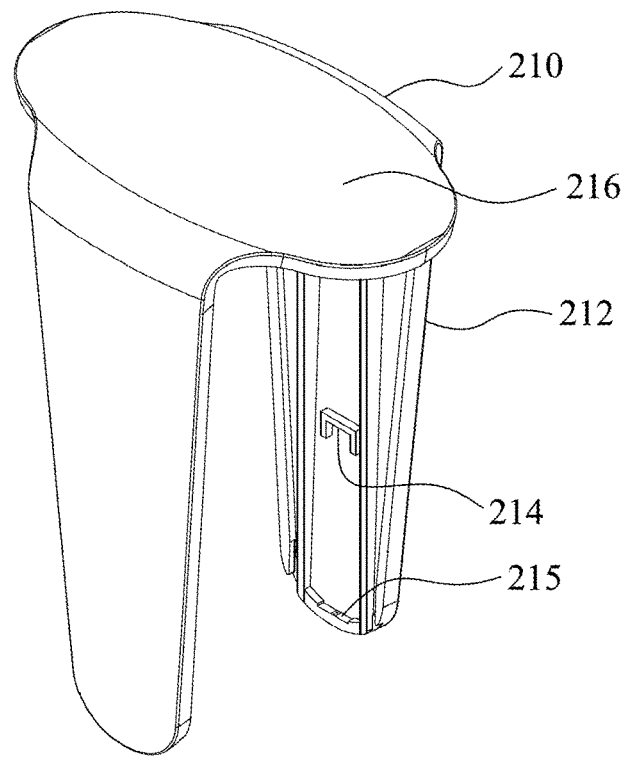
FIG. 3 shows an exploded view of a compression unit of a reduced-pressure device in accordance with an embodiment of the present disclosure.
Figure 3:
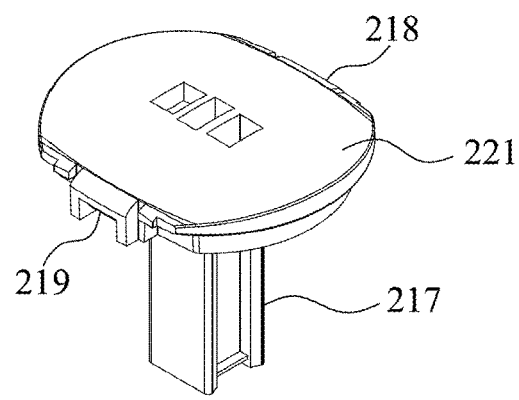
Figure 3:
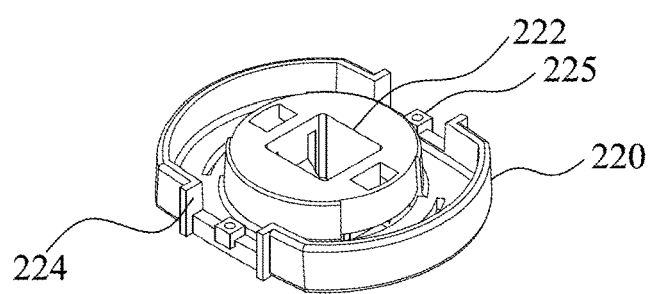
Figure 4:
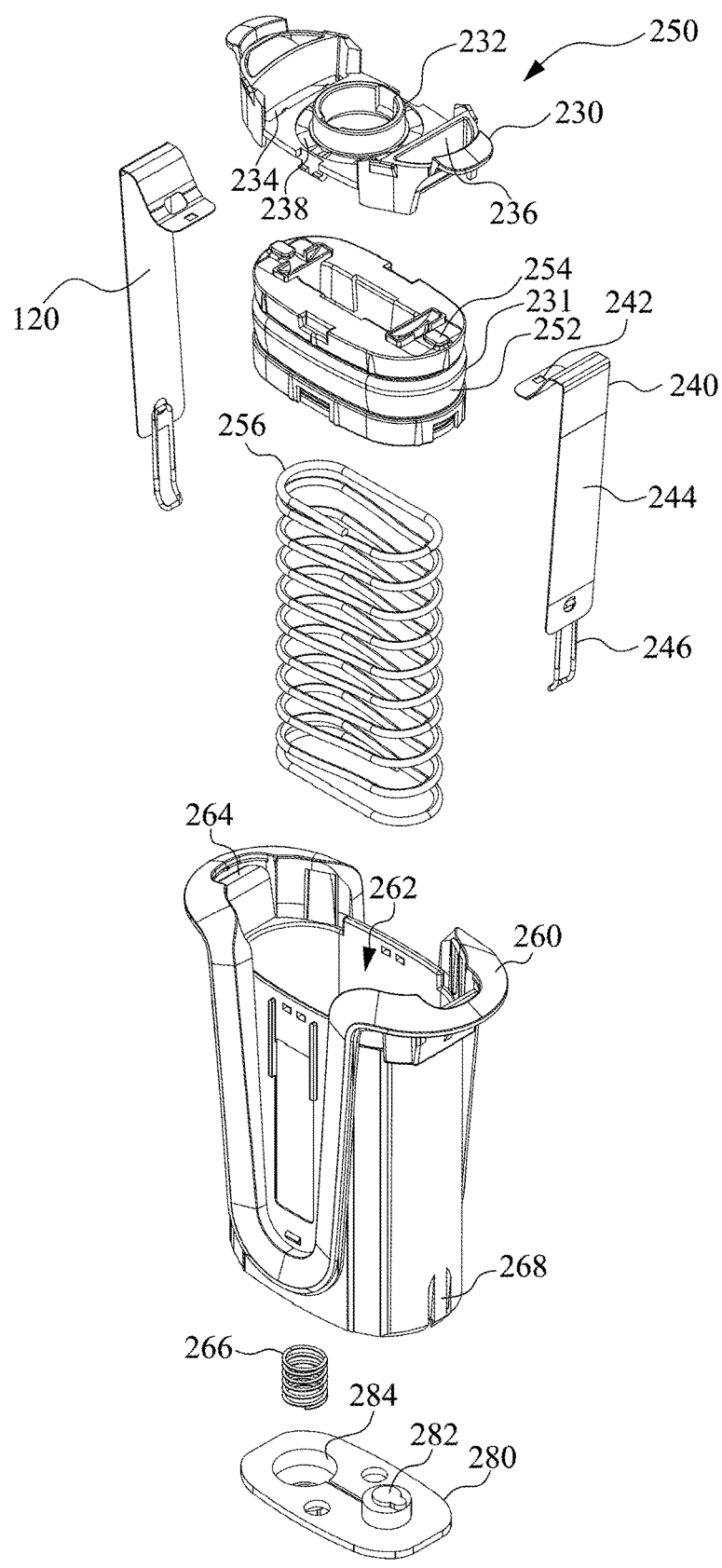
FIG. 4 shows an exploded view of an air pressure storage unit of a reduced-pressure device in accordance with an embodiment of the present disclosure.
Figure 5:
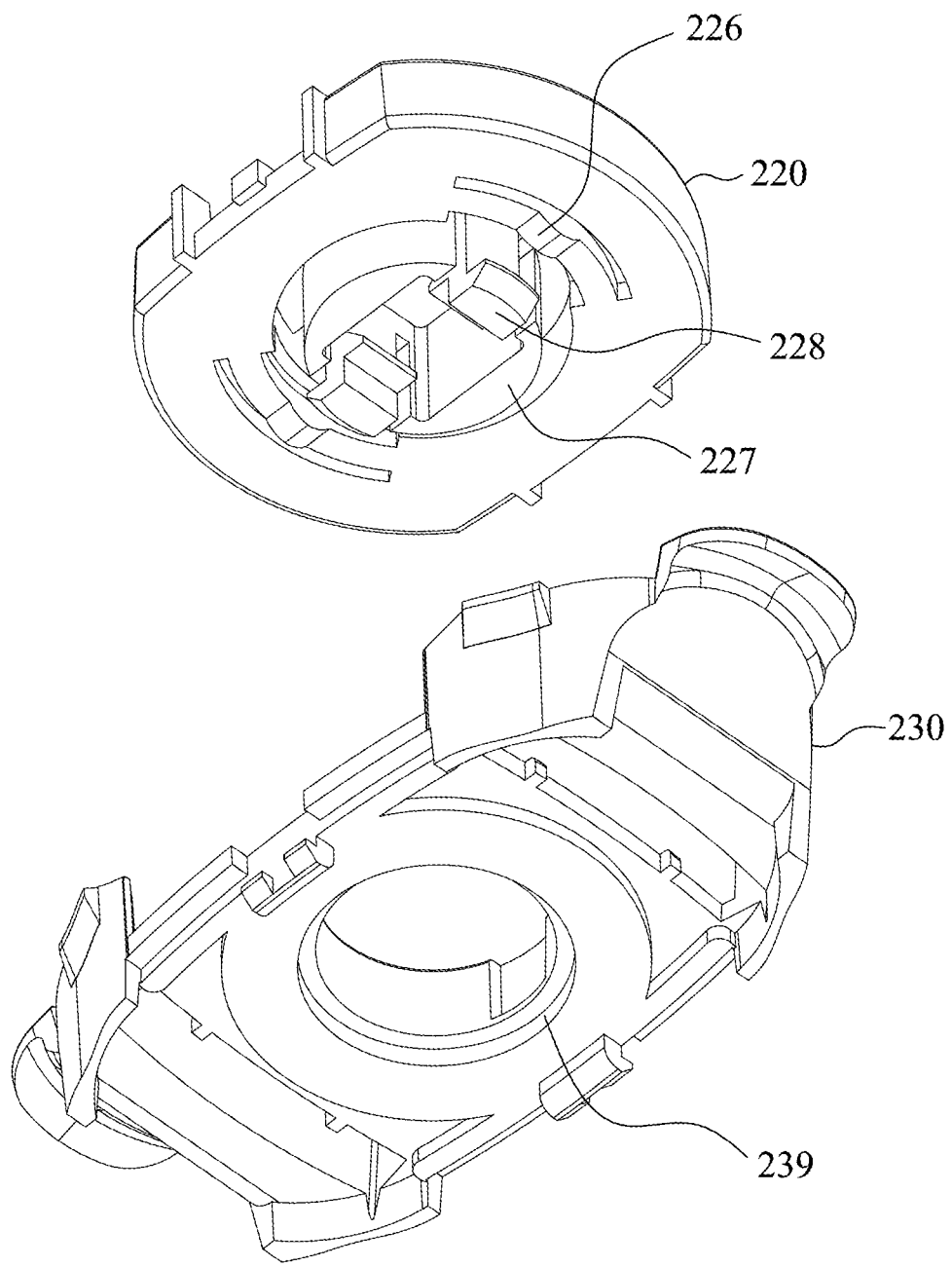
FIG. 5 shows an exploded view of a turntable of the compression unit and a piston assembly of the air pressure storage unit of a reduced-pressure device in accordance with an embodiment of the present disclosure.
Figure 6:
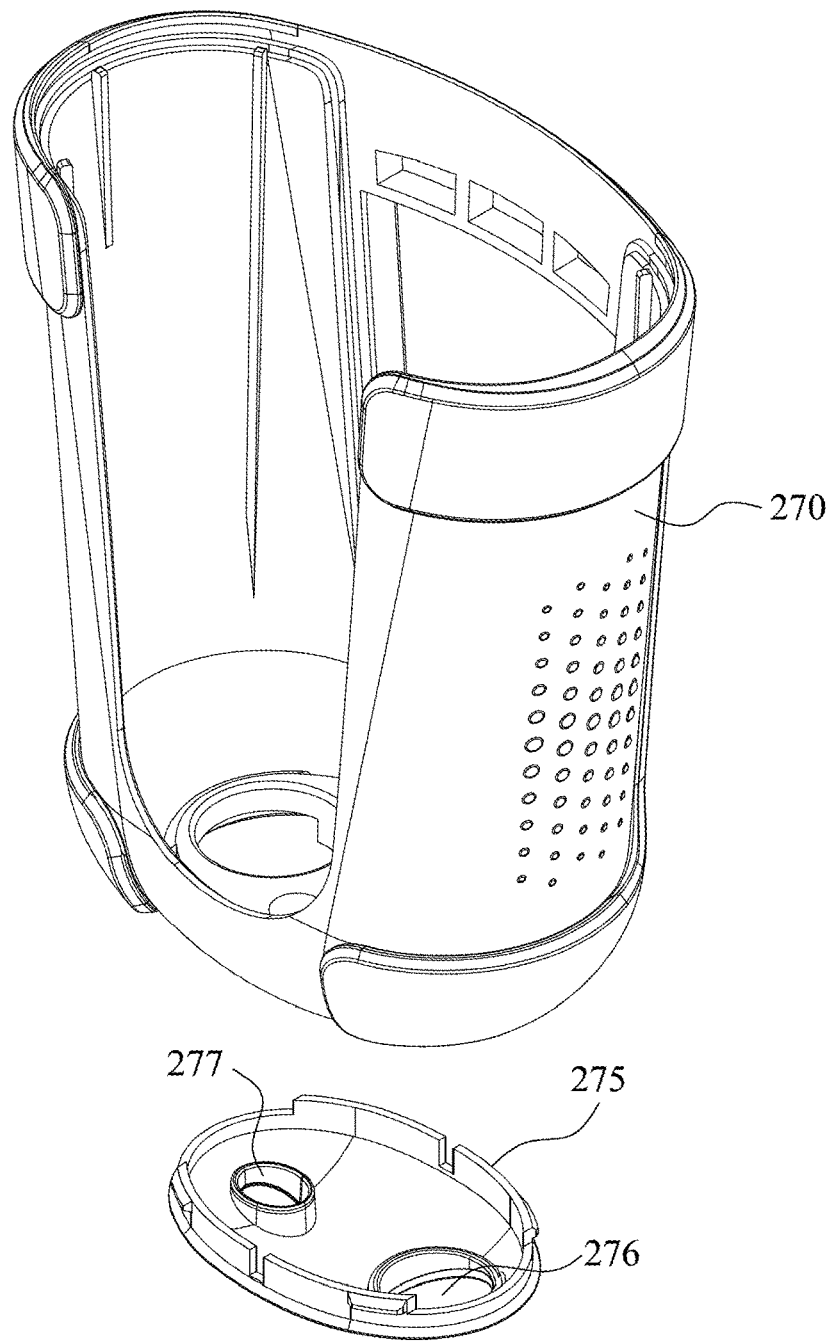
FIG. 6 shows an exploded view of a housing of a reduced-pressure device in accordance with an embodiment of the present disclosure.

Referring to FIG. 3 to FIG. 6, the configuration of the respective components of the reduced-pressure device 100 will be described in more detail. FIG. 3 shows an exploded view of the compression unit 110 of the reduced-pressure device 100. FIG. 4 shows an exploded view of the air pressure storage unit 130 of a reduced-pressure device 100. FIG. 5 shows an exploded view of the turntable 220 of the compression unit 110 and the piston assembly 250 of the air pressure storage unit 130 of a reduced-pressure device 100. FIG. 6 shows an exploded view of the housing 140 of a reduced-pressure device 100.

As shown in FIG. 3, the pressing element 210 further includes a pair of push rods 212 and a pressing portion 216 connecting the push rods. The pressing portion 216 facilitates the user to pull or press the pressing element 210, and the push rods 212 are used for compressing the piston assembly 250.

The extended shaft 217 of the sliding element 218 is used for inserting into a positioning opening 222 of the turntable 220. The extended shaft 217 has a non-circular cross-section, for example, a square, an oval, an I-shaped or a triangular shape, and is not limited thereto, and the positioning opening 222 has a shape corresponding to the cross-section of the extended shaft 217, so that the sliding element 218 can drive the turntable 220 to rotate.

Each of the push rods 212 further comprises a first engaging portion 214 and a second engaging portion 215 at the inner sidewall, and the cap 221 of the sliding element 218 includes a pair of first positioning portions 219, and the turntable 220 includes a pair of second positioning portions 225. When the pressing element 210 is pulled up, the first engaging portion 214 is firstly engaged to the first positioning portion 219 of the cap 221 of the sliding element 218 and pull up the sliding element 218 at the same time, and when the pressing element 210 is pulled up further, the second engaging portion 215 is engaged to the second positioning portion 225 of the turntable, and thus, the pressing element 210 can be prevented from being pulled out of the reduced-pressure device 100. The turntable 220 also has accommodating openings 224 for receiving the first positioning portions 219 when the sliding element 218 is pressed down and stops on the turntable 220.

As shown in FIG. 4, the piston assembly 250 further comprises a piston cover 230 and a piston 231. The piston cover 230 is installed on the pressure storage container 260, and has a pair of push rod openings 234, only one shown in the drawings. The piston 231 is installed in the pressure storage container 260. The air pressure storage unit 130 further comprises a sealing element 280 disposed on the lower part of the pressure storage container 260 to seal the pressure storage container 260. A negative-pressure storage zone 262 is formed between the piston 231 and the sealing element 280 of the pressure storage container 260 accordingly. Referring to both FIG. 3 and FIG. 4, therefore, the push rods 212 of the pressing element 210 can pass through the push rod openings 234 to push the piston 231 of the piston assembly 250 when the pressing element 210 is at the predetermined position to compress the piston spring 256, and after the compression force of the push rods is released, the piston spring 256 generates a recover force for the piston 231 to produce a negative pressure in the container 260.

The piston assembly 250 further comprises a resilient ring 252 and a fixing portion 254, which is a one-way valve of a soft material, for example, an annular check valve of a rubber material.

The sealing element 280 further comprises a check valve 282 for connecting a connecting pipe 150 of a negative-pressure wound dressing to provide a negative pressure for the negative-pressure wound dressing and to avoid the gas backflow to the connecting pipe 150 and the negative-pressure wound dressing.

The sealing element 280 further comprises a working indicator 284 to indicate the negative-pressure state of the pressure storage container 260. The sealing element 280 further comprises a spring 266 disposed between the working indicator 284 and the pressure storage container 260. The spring 266 provides a resilient force, and the resilient force can be set in accordance with the negative-pressure value actually generated in the pressure storage container 260. When the air pressure storage unit 130 is in a negative-pressure state, the suction force of the working indicator 284 can be sucked by the suction of the negative pressure due to the suction force of the negative pressure greater than the resilient force of the spring 266, and when the air pressure storage unit 130 fails to provide sufficient negative pressure, the working indicator 284 protrudes outwardly from the housing 140. Therefore, it is easy for the user to confirm whether the air pressure storage unit 130 is in a negative-pressure state or not by touching the working indicator 284 without watching the reduced-pressure device 100. If there is no sufficient negative pressure, the user can manually compress the air pressure storage unit 130 to produce negative pressure again.

The reduced-pressure device 100 further comprises a pressure indicating module 120. The pressure indicating module 120 includes a pressure indicator 240 having a fixing opening 242, an indicating portion 244, and an elastic member 246. One end of the pressure indicating module 120 is mounted on an indicator engaging portion 268 of the pressure storage container 260, and the other end thereof passed through an opening 264 of the pressure storage container 260 is attached to a fixing portion 254 of the piston assembly 250. The fixing opening 242 is used for engaging the fixing portion 254 of the piston assembly 250, and the indicating portion 244 is marked with the pressure information, such as sections with different colors to indicating different pressure value, or numerical ratios to show the pressure information. The elastic member 246 is, for example, an elastic ring or a spring, and is not limited thereto. The elastic member 246 is coupled to the indicator engaging portion 268 of the pressure storage container 260, so that the elastic member 246 changes its length as the piston assembly 250 moves. The piston cover 230 further comprises a transparent window 236 to expose the pressure indicating module 120. Thus, the user can see the information shown as different colors on the indicating portion 244 or the numerical ratios via the transparent window 236 on the piston cover 230 to be easily aware of how much capacity of negative pressure the current reduced-pressure device 100 can continuously be provided in order to determine when to operate the compression unit 110 again for providing the desired negative pressure.

Referring to FIG. 3, FIG. 4 and FIG. 5, the turntable 220 further includes elastic protrusions 226, a rotating hole 227 and claws 228. The piston cover 230 further includes a rotation shaft 232, a positioning ring 238 and an engaging ring 239. After the turntable 220 is engaged with the lower piston cover 230, the claws 228 of the turntable 220 are snapped against the engaging ring 239 of the piston cover 230 to firmly engage the compression unit 110 with the air pressure storage unit 130 when used. The rotating hole 227 is coupled to the rotation shaft 232, so that the compression unit 110 is rotatable relative to the air pressure storage unit 130. In addition, the elastic protrusions 226 cooperate with the protrusions and recesses formed on the positioning ring 238, so that the compression unit 110 can be correctly positioned at an appropriate position when rotated relative to the air pressure storage unit 130.

As shown in FIG. 6, the housing 140 includes a housing body 270 and a body lower cover 275. The body lower cover 275 includes a connecting pipe opening 276 and an indicator opening 277, so that the connecting pipe 150 can be connected to the air pressure storage unit 130 and the working indicator 284 can also be exposed by the indicator opening 277.

Figure 2B:
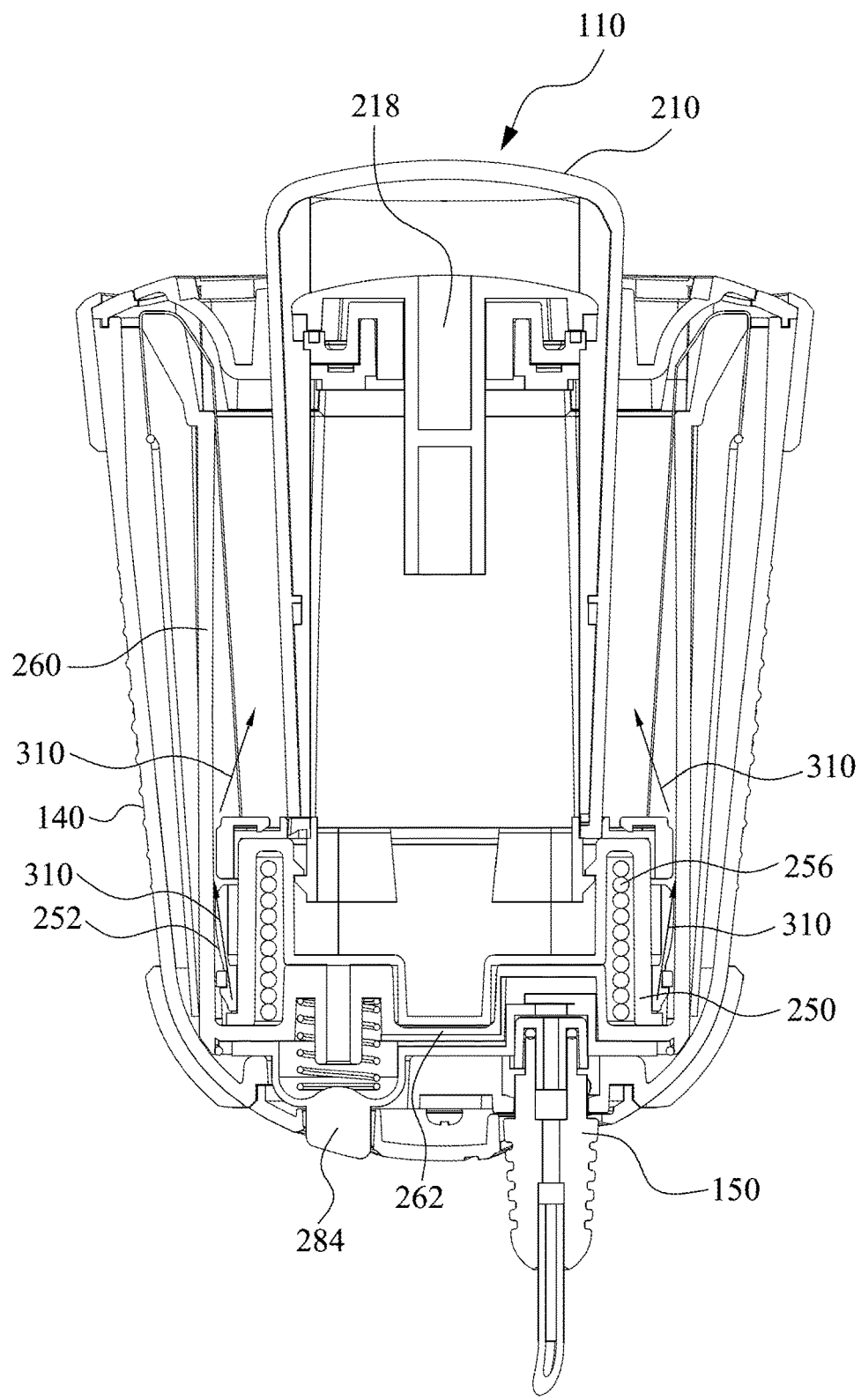
FIG. 2B shows a cross-sectional perspective view of a reduced-pressure device when the compression unit is rotated to a predetermined position and pressed down to compress the air pressure storage unit in FIG. 2A.
Figure 2C:
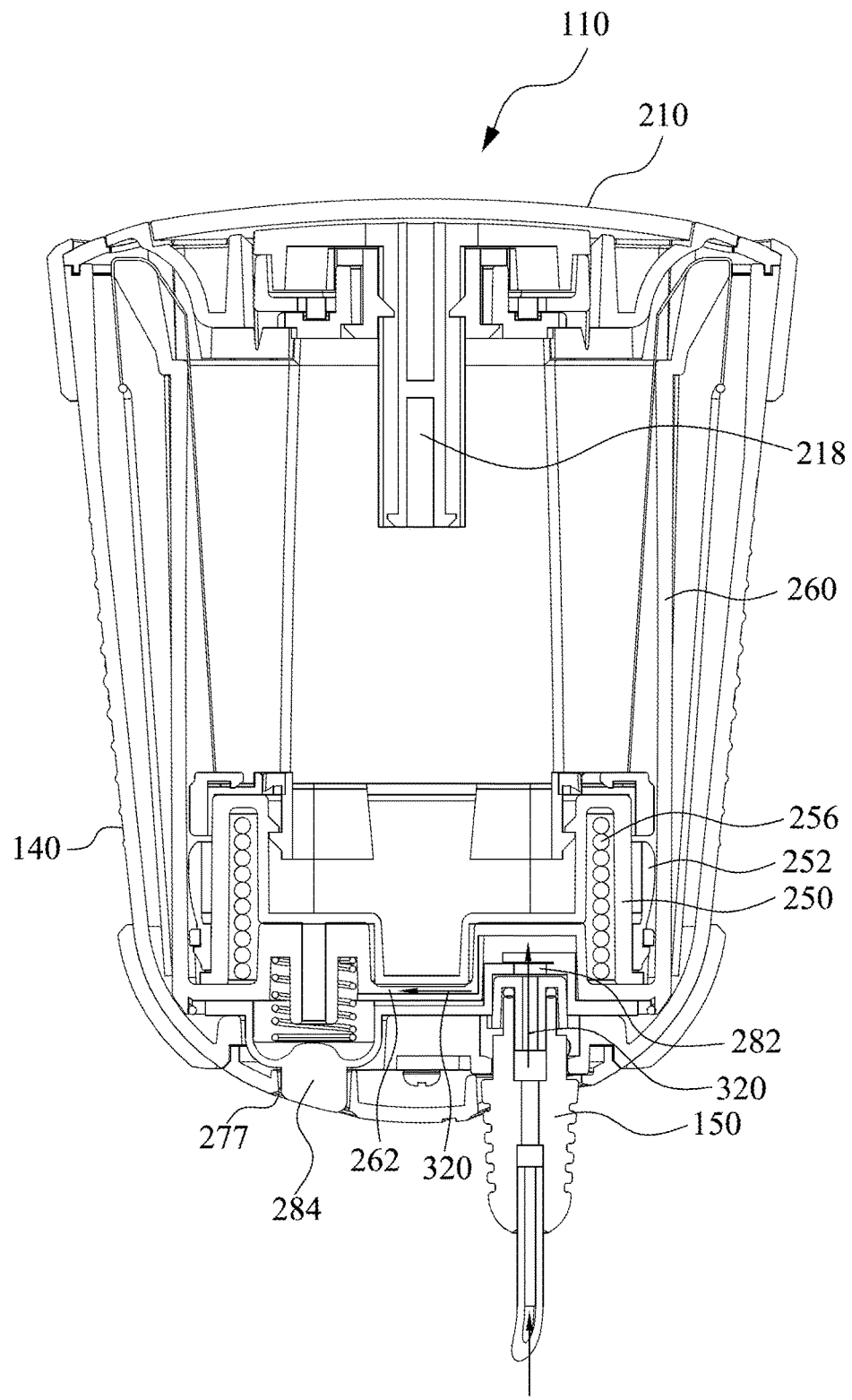
FIG. 2C shows a cross-sectional perspective view of a reduced-pressure device when the pressing element is returned to the recesses of housing and the air pressure storage unit is started in FIG. 2A.

Referring to FIG. 2A to FIG. 2C, FIG. 2A to FIG. 2C also demonstrate how the reduced-pressure device 100 operates to form a negative pressure in the negative-pressure storage zone 262 of the pressure storage container 260. FIG. 2B shows a cross-sectional perspective view of a reduced-pressure device 100 when the compression unit 110 is rotated to a predetermined position and pressed down to compress the air pressure storage unit 130; FIG. 2C shows a cross-sectional perspective view of a reduced-pressure device 100 when the pressing element 210 is returned to the recesses 160 of housing 140 and the air pressure storage unit 130 is started.

As shown in FIG. 2A, the reduced-pressure device 100 is not yet started, and the compression unit 110 is coupled to the housing 140, and the piston spring 256 is in a relaxed state, so that the piston assembly 250 is located in the upper portion of the pressure storage container 260.

When push the piston 231 of the piston assembly 250 with the compression unit 110 to discharge the air in the negative-pressure storage zone 262 in the pressure storage container 260, as shown in FIG. 2B, the compression unit 110, which has been rotated about 90 degrees, is pressed down to move the piston 231 downward and compress the piston spring 256. The air originally in the negative-pressure storage zone 262 is discharged to the other side of the piston assembly 250 via the resilient ring 252 of the piston assembly 250, with reference to the direction indicated by the arrow 310.

As shown in FIG. 2C, the user can recover the compression unit 110 to the original accommodated position and fasten it over the housing 140, and the resilient force generated by the compressed piston spring 256 causes a negative pressure in the negative-pressure storage zone 262 to suck the air in the negative-pressure wound dressing into the negative-pressure storage zone 262 via the connecting pipe 150 and the check valve 282, with reference to the direction indicated by the arrow 320.

While the disclosure has been described by way of example(s) and in terms of the preferred embodiment(s), it is to be understood that the disclosure is not limited thereto. On the contrary, it is intended to cover various modifications and similar arrangements and procedures, and the scope of the appended claims therefore should be accorded the broadest interpretation so as to encompass all such modifications and similar arrangements and procedures.

What is claimed is:

1. A reduced-pressure device for wound treatment comprising:
    a housing having recesses on sidewalls thereof;
    an air pressure storage unit installed in the housing, comprising:
        a pressure storage container;
        a piston assembly slidably installed in the pressure storage container; and
        a piston spring installed between the base of the pressure storage container and the piston assembly; and
    a compression unit mounted on the piston assembly of the air pressure storage unit, including a pressing element and a turntable, wherein for generating a negative pressure, the pressing element is pulled out of the recesses and rotated to a predetermined position, the pressing element is pressed down into an opening formed in a piston cover to compress the piston assembly down to generate the negative pressure in the pressure storage container and the pressing element is pulled up again and rotated back to an original position for being accommodated into the recesses.

2. The reduced-pressure device of claim 1, wherein the compression unit further comprises a sliding element connected to the pressing element and to the turntable to stabilize a movement between the pressing element and the turntable and simultaneously rotate the turntable.

3. The reduced-pressure device of claim 2, wherein the pressing element further includes a pair of push rods and a pressing portion connecting the push rods, wherein each of the push rods further comprises a first engaging portion and a second engaging portion, and the sliding element includes a cap and an extended shaft, wherein the cap has a pair of first positioning portions for engaging with the first engaging portion of each push rods, and the turntable includes a pair of second positioning portions for engaging with the second engaging portion of each push rod, and when the first engaging portion of each push rods is coupled to the first positioning portion of the sliding element, the pressing element can pull the sliding element at the same time, and when the second engaging portion of each of the push rods is coupled to the second positioning portion of the turntable respectively, the pressing element can be prevented from being pulled out of the reduced-pressure device.

4. The reduced-pressure device of claim 3, wherein the piston assembly further comprises a piston, and the opening formed in the piston cover comprises a pair of push rod openings, and the push rods of the pressing element can pass through the push rod openings to push the piston of the piston assembly when the pressing element is positioned at the predetermined position.

5. The reduced-pressure device of claim 4, wherein the air pressure storage unit further comprises a sealing element to seal the pressure storage container.

6. The reduced-pressure device of claim 5, wherein the sealing element further comprises a check valve for connecting a connecting pipe of a negative-pressure wound dressing.

7. The reduced-pressure device of claim 6, wherein the sealing element further comprises a working indicator to indicate a negative-pressure state in the air pressure storage unit.

8. The reduced-pressure device of claim 4, further comprising a pressure indicating module engaged to the pressure storage container and the piston assembly.

9. The reduced-pressure device of claim 8, wherein the piston cover further comprises a transparent window to expose the pressure indicating module.

* * * * *